United States Patent
Gattiker et al.

(10) Patent No.: US 10,737,114 B2
(45) Date of Patent: Aug. 11, 2020

(54) TRANSLATING DIFFERENT CLINICAL PROTOCOLS FOR PARTICLE THERAPY INTO A SET OF CONSTRAINTS

(71) Applicant: INTERNATIONAL BUSINESS MACHINES CORPORATION, Armonk, NY (US)

(72) Inventors: Anne E. Gattiker, Austin, TX (US); Sani R. Nassif, Austin, TX (US); Tom Osiecki, Austin, TX (US); Chin Ngai Sze, Austin, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 910 days.

(21) Appl. No.: 15/370,885

(22) Filed: Dec. 6, 2016

(65) Prior Publication Data

US 2018/0154176 A1 Jun. 7, 2018

(51) Int. Cl.
*A61F 5/10* (2006.01)
*A61N 5/10* (2006.01)

(52) U.S. Cl.
CPC .......... *A61N 5/1031* (2013.01); *A61N 5/1071* (2013.01); *A61N 2005/1087* (2013.01)

(58) Field of Classification Search
CPC ............... A61N 5/1039; A61N 5/1077; A61N 2005/1087; A61N 5/103; A61N 5/1084; A61N 2005/1089
USPC .......................................................... 600/1–8
See application file for complete search history.

(56) References Cited

U.S. PATENT DOCUMENTS

| 6,546,073 | B1 * | 4/2003 | Lee ...................... A61N 5/1031 378/65 |
| 8,986,186 | B2 | 3/2015 | Zhang et al. |
| 2014/0350322 | A1 * | 11/2014 | Schulte ................ A61N 5/1039 600/1 |
| 2017/0028220 | A1 * | 2/2017 | Schulte ................ A61N 5/1042 |

OTHER PUBLICATIONS

Bednarz, Ph.D., Bryan, "Monte Carlo Methods in Proton Therapy," Oct. 2005, Powerpoint Presentation (39 pages).
Paganetti, Harald et al., "Proton Beam Radiotherapy—The State of the Art," New Technologies in Radiation Oncology (Medical Radiology Series), Oct. 2005, pp. 1-36, Massachusetts General Hospital, Boston, MA, USA.

(Continued)

*Primary Examiner* — Samuel G Gilbert
(74) *Attorney, Agent, or Firm* — Tutunjian & Bitetto, P.C.; Brian Welle

(57) ABSTRACT

A method and system are provided for converting clinical criteria constraints for a target structure of radiation therapy into a second set of constraints. The method includes selecting, by a hardware processor, a plurality of clusters of voxels in the target structure based on pre-specified criteria. The method further includes assigning, by the hardware processor, each of the plurality of clusters of voxels a respective constraint that specifies one or more bounds on a radiation dose applied to each voxel in a corresponding one of the plurality of clusters of voxels. The method also includes storing, in a memory device, the respective constraint for each of the plurality of clusters of voxels.

20 Claims, 6 Drawing Sheets

(56) References Cited

OTHER PUBLICATIONS

Li, Yupeng et al., "An efficient dose calculation strategy for intensity modulated proton therapy," Physics in Medicine and Biology, Jan. 2011, pp. N71-N84, Phys. Med. Biol. 56 (2011), 2011 Institute of Physics and Engineering in Medicine.

Ericsson, Malin, "Intensity Modulated Proton Therapy (IMPT)—A comparative treatment planning study," Master of Science Thesis, Jan. 2007, pp. 1-76, Department of Radiation Physics, Lund University Hospital, Medical Radiation Physics Clinical Sciences, Lund, Lund University.

Breedveld, Sebastiaan et al., "A novel approach to multi-criteria inverse planning for IMRT," Physics in Medicine and Biology, Oct. 2007, pp. 6339-6353, Phys. Med. Biol. 52 (2007), 2007 IOP Publishing Ltd.

Gonzalo, Cabal et al., "Target Definition and Treatment Planning in Particle Therapy using Monte Carlo Error Propagation Analysis," Powerpoint Presentation, 1st New Mexico Workshop on Monte Carlo for Particle Therapy Treatment Planning Albuquerque, New Mexico May 16-18, 2011 (45 pages).

Chen, Wei et al., "A fast optimization algorithm for multicriteria intensity modulated proton therapy planning," American Association of Physicists in Medicine, Aug. 2010, pp. 4938-4945, Med. Phys. 37 (9).

Chvetsov, Alexei V. et al., "Regularization of inverse planning for intensity-modulated radiotherapy," American Association of Physicists in Medicine, Jan. 2005, pp. 501-514, Med. Phys. 32 (2).

Gui, Yi et al., "Constrained Grouped Sparsity," Conference Paper, Dec. 2012, pp. 1-27, Proceedings of the 25th Australasian joint conference on Advances in Artifcial Intelligence.

Fredricksson, Albin, "Automated Improvement of Radiation Therapy Treatment Plans by Optimization Under Reference Dose Constraints," Physics in Medicine and Biology 57, Nov. 2012, pp. 7799-7811.

Friedman, Jerome et al., "A note on the group lasso and a sparse group lasso," arXiv preprint arXiv, Jan. 2010, pp. 1-8, 1001.0736.

Holdsworth, Clay et al., "The use of a multiobjective evolutionary algorithm to increase flexibility in the search for better IMRT plans," American Association of Physicists in Medicine, Apr. 2012, pp. 2261-2274, Med. Phys. 39 (4).

Petit, Steven et al., "Increasing maximum tumor dose to manage range uncertainties in IMPT treatment planning," Physics in Medicine and Biology, Sep. 2013, pp. 7329-7341, Phys. Med. Biol. 58 (2013), 2013 Institute of Physics and Engineering in Medicine.

Lim, Gino J. et al., "A two-phase method for selecting IMRT treatment beam angles: Branch-and-Prune and local neighborhood search," European Journal of Operational Research, Feb. 2012, pp. 609-618, 217 (3).

Li, Gino J. et al., "Iterative Solution Methods for Beam Angle and Fluence Map Optimization in Intensity Modulated Radiation Therapy Planning," OR Spectrum, Apr. 2008, pp. 289-309, 30 (2).

Unkelbach, Jan et al., "The dependence of optimal fractionation schemes on the spatial dose distribution," Physics in medicine and biology, Dec. 2012, pp. 1-14, 58(1) 159.

Chen, Wei et al., "Including Robustness in Multi-criteria Optimization for Intensity Modulated Proton Therapy," Department of Radiation Oncology, Massachusetts General Hospital and Harvard Medical School, Dec. 2011, pp. 1-17, arXiv 1112.5362 v1.

Craft, David L. et al., "Approximating convex Pareto surfaces in multiobjective radiotherapy planning," American Association of Physicists in Medicine, Aug. 2006, pp. 3399-3407, Med. Phys. 33 (9).

Fredriksson, Albin et al., "Minimax optimization for handling range and setup uncertainties in proton therapy," American Association of Physicists in Medicine, Mar. 2011, pp. 1672-1684, Med. Phys. 38 (3).

Paganetti, Harald, "Range uncertainties in proton therapy and the role of Monte Carlo simulations," Phys Med Biol. Jun. 2012, pp. 1-27, 57 (11).

Cao, Wenhua et al., "Beam angle selection in Intensity Modulated Proton Therapy treatment planning for prostate cancer," Proceedings of the 2011 Industrial Engineering Research Conference, Jan. 2011, pp. 2-8.

Siebers, Ph.D, Jeffrey V. et al., "Monte Carlo Applications in IMRT Planning and Quality Assurance," Proceedings of the 2006 AAPM Summer School, edited by I. Chetty (Medical Physics Publishing Corp, Madison, WI, 2006), Jun. 2006, pp. 1-33.

Iordache, Marian-Daniel et al., "Hyperpectral Unmixing with Sparse Group Lasso," Geoscience and Remote Sensing Symposium (IGARSS), Oct. 2011, pp. 3586-3589, 2011 IEEE International.

Kim, Taeho et al., "Inverse planning for IMRT with nonuniform beam profiles using total-variation regularization (TVR)," American Association of Physicists in Medicine, Dec. 2010, pp. 57-66, Med. Phys. 38 (1).

Zhu, Lei et al., "Using total-variation regularization for intensity modulated radiation therapy inverse planning with field-specific numbers of segments," Phys. Med. Biol., Nov. 2008, pp. 6653-6672, 53 (2008).

Tibshirani, Robert, "Regression shrinkage and selection via the lasso: a retrospective," Journal of the Royal Statistical Society, Sep. 2011, pp. 273-282, B (2011) 73, Part 3.

Simon, Noah et al., "Standardization and the Group Lasso Penalty," Statistica Sinica, Jul. 2012, pp. 1-21.

Unkelbach, Jan et al., "Reducing the sensitivity of IMPT treatment plans to setup errors and range uncertainties via probabilistic treatment planning," American Association of Physicists in Medicine, Dec. 2008, pp. 149-164, Med. Phys. 36 (1).

Xia, Ph. D, Ping, "Inverse Planning Techniques for IMRT," Powerpoint Presentation, Jul. 2004, (22 pages).

Liu, Wei et al., "Effectiveness of robust optimization in intensity-modulated proton therapy planning for head and neck cancers," American Association of Physicists in Medicine, Apr. 2013, pp. 051711-1-051711-9, Med. Phys. 40 (5).

Cao, Wenhua et al., "Proton energy optimization and reduction for intensity-modulated proton therapy," Phys Med Biol., Nov. 2014, pp. 6341-6354, 59 (21).

Cao, Wenhua et al., "Incorporating deliverable monitor unit constraints into spot intensity optimization in intensity modulated proton therapy treatment planning," Phys Med Biol., Aug. 2013, pp. 5113-5125, 58 (15).

Liu, Wei et al., "Robust optimization of intensity modulated proton therapy," American Association of Physicists in Medicine, Feb. 2012, pp. 1079-1092, Med. Phys. 39 (2).

Yuan, Ming et al., "Model selection and estimation in regression with grouped variables," J. R. Statist, Nov. 2006, pp. 49-67, Soc. B (2006) 68, Part 1.

\* cited by examiner

TRANSLATING DIFFERENT CLINICAL PROTOCOLS FOR PARTICLE THERAPY INTO A SET OF CONSTRAINTS

BACKGROUND

Technical Field

The present invention relates generally to particle therapy and, in particular, to translating different clinical protocols for particle therapy into a set of constraints.

Description of the Related Art

Radiation therapy uses high-energy radiation to kill cancer cells by damaging their DNA. Using beams of accelerated protons or heavier ions such as carbon, oncologists can deliver cell-killing energy to precisely targeted tumors and do so without causing extensive damage to surrounding healthy tissue, thus eliminating the major drawback of conventional radiation therapy using x-rays. Particle Beam Cancer Therapy Planning involves finding the appropriate set of radiation settings to deliver the desired radiation dose to each target structure. Hence, radiation treatment planning can involve choosing the energies of the proton beams that are shot into patient, as well as the angles from which they are shot.

Planning is usually done using the outputs of a particle simulator. The outputs indicate the location(s) in a patient's body where candidate protons, having different energies and shot from different angles, drop their energy. A solution to the treatment planning problems determines, using those outputs and a knowledge of the target energies desired in each body region, for each energy level and for each angle, for what duration to shoot protons at a given current.

As a simplified example, consider the case where the desired radiation dose to be delivered to at least 95% of a cancer target structure is 78 Gy, with a constraint of the maximum dose in the heart being 20 Gy. "Clinical Criteria" or "Clinical Protocol" expresses the desired result. In an actual case, some clinical protocols use Cobalt Gray Equivalent (CGE) to define the dose.

While the clinical criteria/protocol can be readily determined, there is a need to simplify the clinical criteria/protocol into a set of minimum-maximum constraints.

SUMMARY

According to an aspect of the present principles, a method is provided for converting clinical criteria constraints for a target structure of radiation therapy into a second set of constraints. The method includes selecting, by a hardware processor, a plurality of clusters of voxels in the target structure based on pre-specified criteria. The method further includes assigning, by the hardware processor, each of the plurality of clusters of voxels a respective constraint that specifies one or more bounds on a radiation dose applied to each voxel in a corresponding one of the plurality of clusters of voxels. The method also includes storing, in a memory device, the respective constraint for each of the plurality of clusters of voxels.

According to another aspect of the present principles, a computer program product is provided for converting clinical criteria constraints for a target structure of radiation therapy into a second set of constraints. The computer program product includes a computer readable storage medium having program instructions embodied therewith. The program instructions are executable by a computer to cause the computer to perform a method. The method includes selecting, by a hardware processor, a plurality of clusters of voxels in the target structure based on pre-specified criteria. The method further includes assigning, by the hardware processor, each of the plurality of clusters of voxels a respective constraint that specifies one or more bounds on a radiation dose applied to each voxel in a corresponding one of the plurality of clusters of voxels. The method also includes storing, in a memory device, the respective constraint for each of the plurality of clusters of voxels.

According to yet another aspect of the present principles, a system is provided for converting clinical criteria constraints for a target structure of radiation therapy into a second set of constraints. The system includes a hardware processor for selecting a plurality of clusters of voxels in the target structure based on pre-specified criteria, and assigning each of the plurality of clusters of voxels a respective constraint that specifies one or more bounds on a radiation dose applied to each voxel in a corresponding one of the plurality of clusters of voxels. The system further includes a memory device for storing the respective constraint for each of the plurality of clusters of voxels.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

The present principles are directed to translating different clinical protocols for particle therapy into a set of constraints. In an embodiment, the present principles translate different clinical protocols into one or more sets of minimum-maximum constraints. A minimum-maximum constraint sets an upper bound (maximum constraint) and a lower bound (minimum constraint) on a value of a radiation dose. The constraint expresses a bound on the total radiation dose to a voxel during treatment according to a treatment plan. Dose can vary by voxel within a target structure. Accordingly, different clusters of voxels in a given target structure can have different minimum-maximum constraints.

In one or more embodiment, the term "minimum-maximum constraints" refers to constraints that set a minimum and maximum. A minimum-only constraint can be thought of as a minimum-maximum constraint where the maximum is infinity. Similarly, a maximum-only constraint can be thought of as a minimum-maximum constraint where the minimum is zero. A minimum-maximum constraint can have a minimum equal to zero and a maximum equal to infinity, which covers the case where no finite bound is needed.

Figure 1:
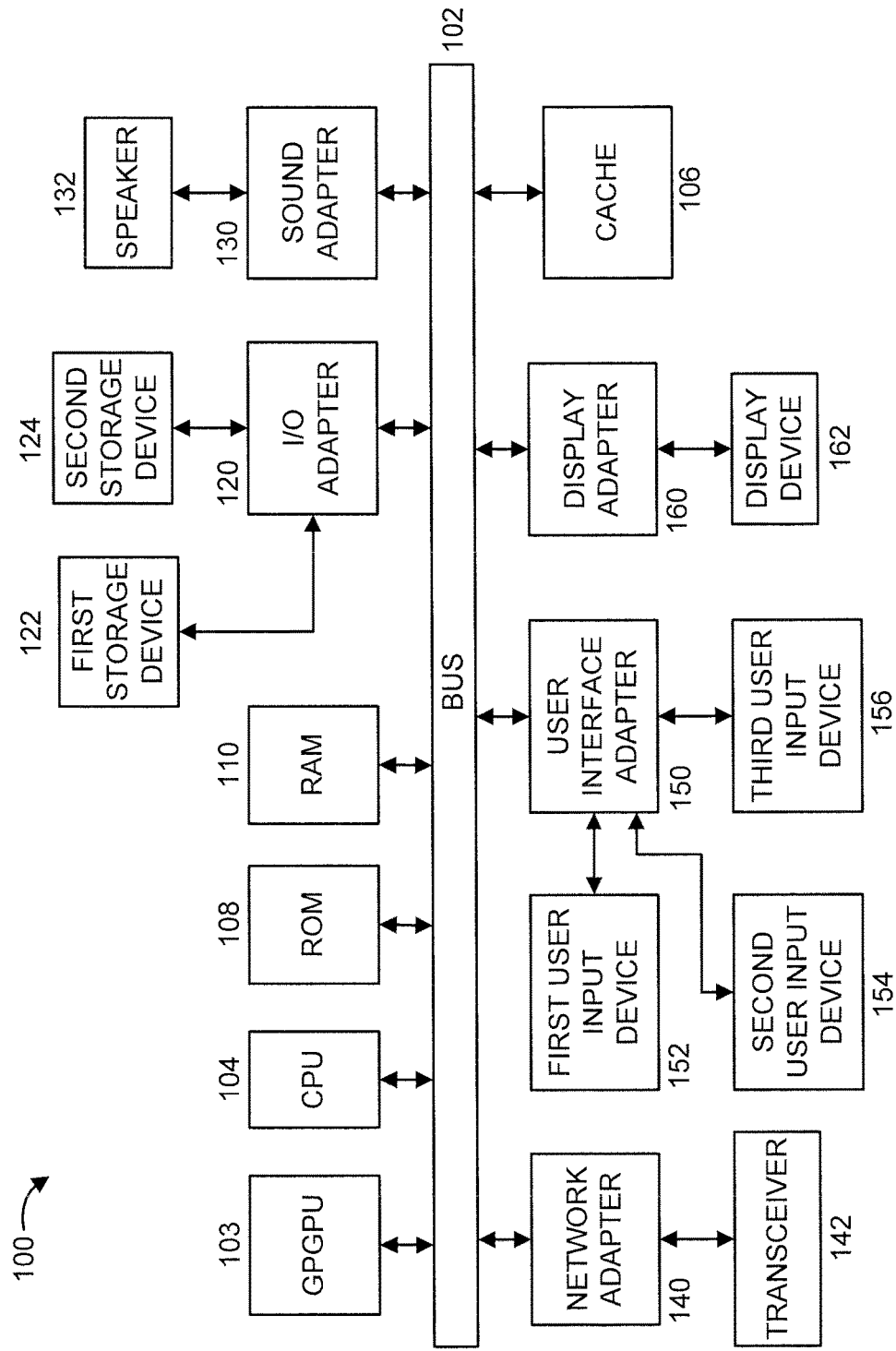
FIG. 1 shows an exemplary processing system 100 to which the present principles may be applied, in accordance with an embodiment of the present principles.

FIG. 1 shows an exemplary processing system 100 to which the present principles may be applied, in accordance with an embodiment of the present principles. The processing system 100 includes at least one processor (CPU) 104 operatively coupled to other components via a system bus 102. A cache 106, a Read Only Memory (ROM) 108, a Random Access Memory (RAM) 110, an input/output (I/O) adapter 120, a sound adapter 130, a network adapter 140, a user interface adapter 150, and a display adapter 160, are operatively coupled to the system bus 102.

A first storage device 122 and a second storage device 124 are operatively coupled to system bus 102 by the I/O adapter 120. The storage devices 122 and 124 can be any of a disk storage device (e.g., a magnetic or optical disk storage device), a solid state magnetic device, and so forth. The storage devices 122 and 124 can be the same type of storage device or different types of storage devices.

A speaker 132 is operatively coupled to system bus 102 by the sound adapter 130. A transceiver 142 is operatively coupled to system bus 102 by network adapter 140. A display device 162 is operatively coupled to system bus 102 by display adapter 160.

A first user input device 152, a second user input device 154, and a third user input device 156 are operatively coupled to system bus 102 by user interface adapter 150. The user input devices 152, 154, and 156 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 152, 154, and 156 can be the same type of user input device or different types of user input devices. The user input devices 152, 154, and 156 are used to input and output information to and from system 100.

Of course, the processing system 100 may also include other elements (not shown), as readily contemplated by one of skill in the art, as well as omit certain elements. For example, various other input devices and/or output devices can be included in processing system 100, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 100 are readily contemplated by one of ordinary skill in the art given the teachings of the present principles provided herein.

Figure 2:
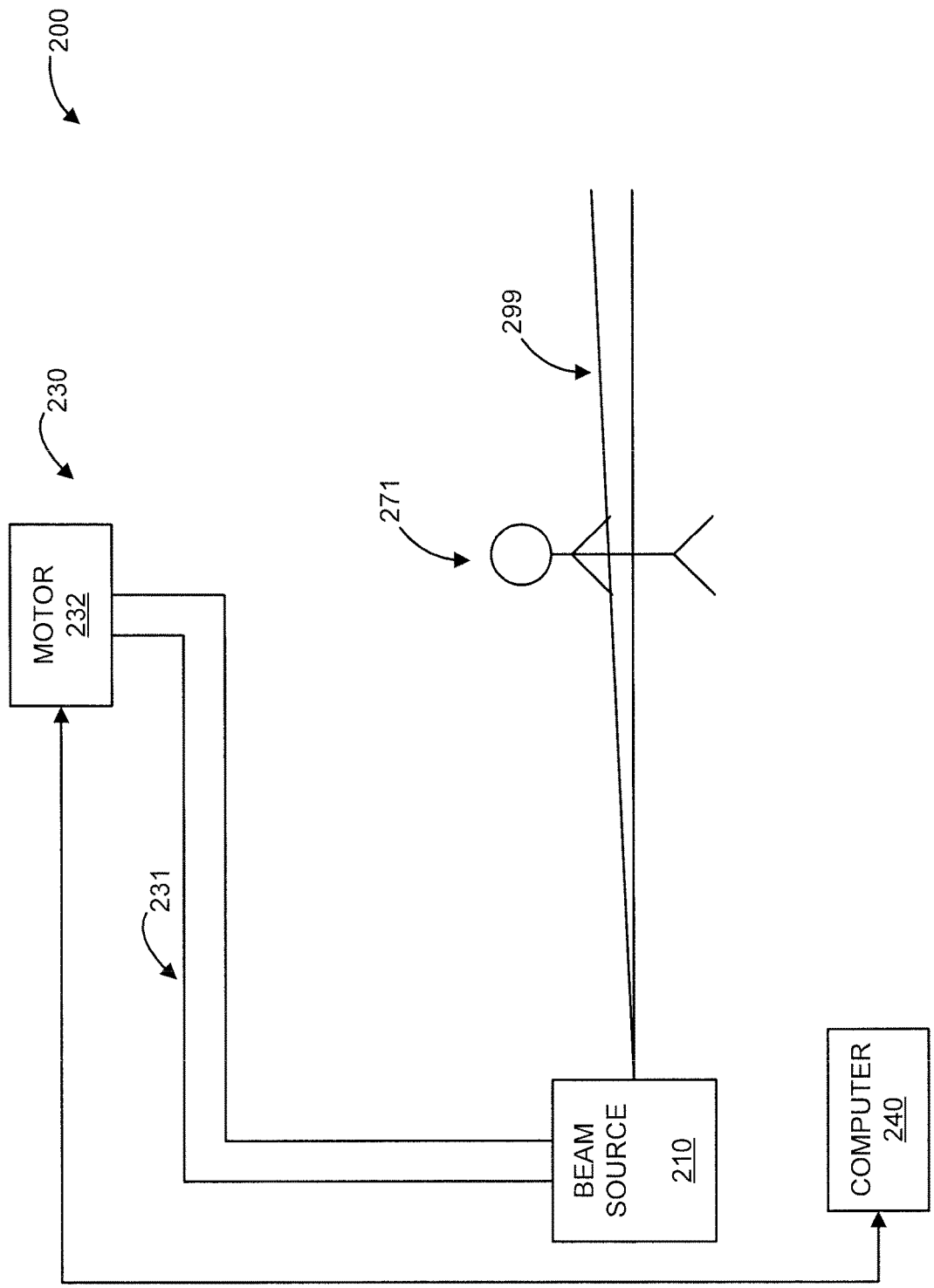
FIG. 2 shows an exemplary radiation therapy system 200 to which the present principles can be applied, in accordance with an embodiment of the present principles.

Moreover, it is to be appreciated that system 200 described below with respect to FIG. 2 is a system for implementing respective embodiments of the present principles. Part or all of processing system 100 may be implemented in one or more of the elements of system 200.

Figure 3:
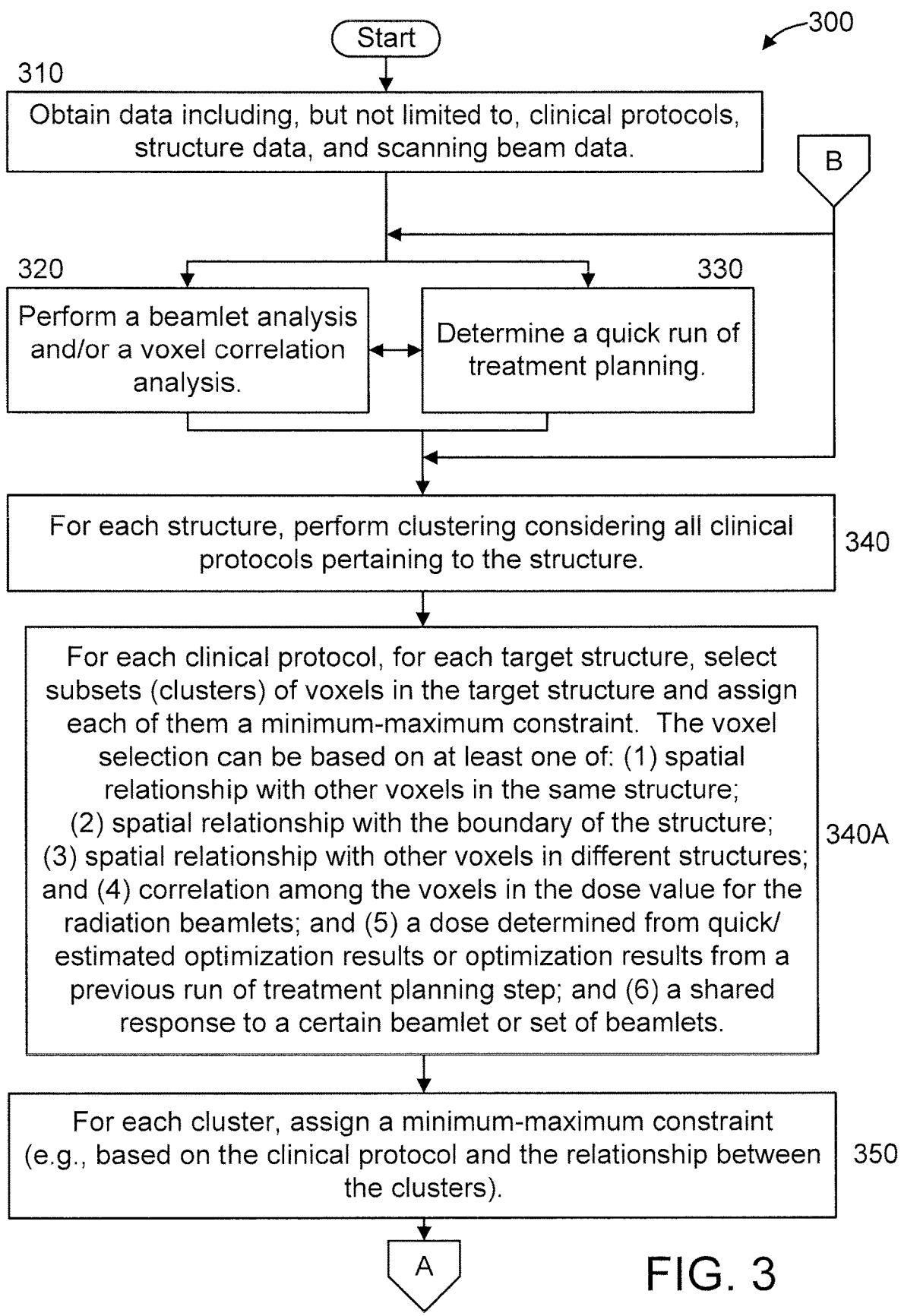
FIGS. 3-4 show an exemplary method 300 for translating different clinical protocols for particle therapy into a set of constraints, in accordance with an embodiment of the present principles.
Figure 4:
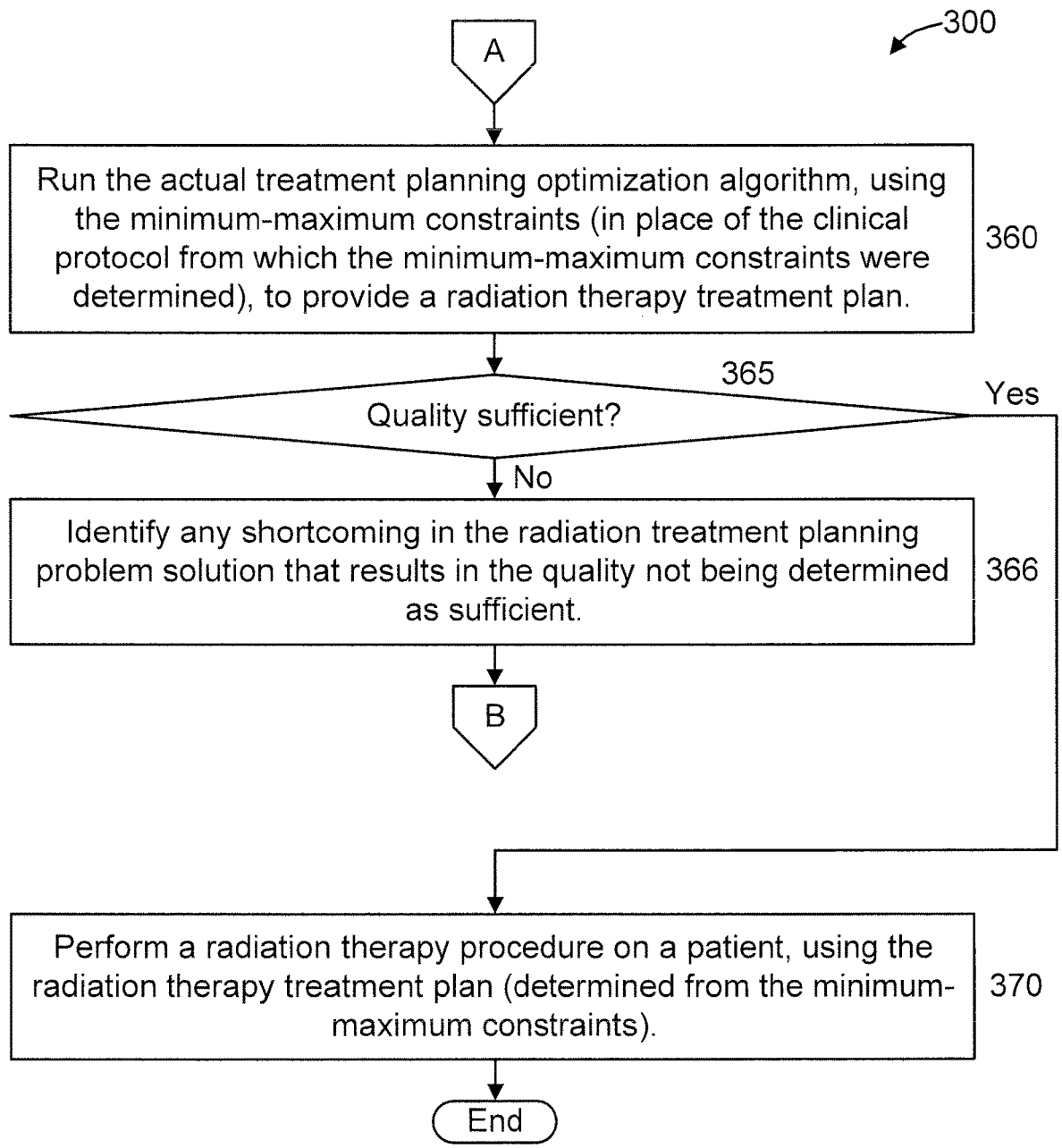

Further, it is to be appreciated that processing system 100 may perform at least part of the method described herein including, for example, at least part of method 300 of FIGS. 3-4. Similarly, part or all of system 200 may be used to perform at least part of method 300 of FIGS. 3-4.

FIG. 2 shows an exemplary radiation therapy system 200 to which the present principles can be applied, in accordance with an embodiment of the present principles.

The radiation therapy system 200 includes a beam source 210, a positional device 230, and a computer 240.

The beam source 210 provides a radiation source for emitting radiation 299 to a target structure. In an embodiment, the beam source 210 can include a particle accelerator. In an embodiment, the beam source generates beamlets. Assuming proton pencil beam therapy, a beamlet is a stream of protons of a given energy shot from a given angle at a given location in a scan matrix.

The positional device 230 is attached to and positions the beam source 210 relative to an object of interest (person) 271 to emit radiation to one or more target structures (e.g., cancer tumors) in the object of interest. Often, the positional device 230 includes a structural member 231 to secure the beam source 210 for positioning, and a motor 232 to position the structural member 231 with respect to the one or more target structures.

The computer 240 controls the elements of system 200. For example, the computer 240 activates the beam source 210, and controls the movement of the positional device 230. Wiring for such control can be within the structural member 231 or in some other arrangement. The computer 240 includes a processor 240A and a memory 240B. The processor 240A initiates the controlling of the other elements including, for example, the emission of radiation by the beam source 210. The memory 240B stores software for performing a radiation therapy process. The memory 240B can also store data generated during a radiation therapy process.

It is to be appreciated that the present principles are not dependent upon any particular type of radiation therapy system and, thus, can be used with any type of radiation therapy system, while maintaining the spirit of the present principles. Thus, it is to be further appreciated that system 200 is generally described and can include other elements and other capabilities, as readily recognized by one of ordinary skill in the art. Moreover, while system 200 is described in one embodiment as involving protons, systems employing other types of radioactive elements can also be used in accordance with the teachings of the present principles, while maintaining the spirit of the present principles. These and other variations of system 200, as well as other radiation therapy systems to which the present principles can be applied, are readily determined by one of ordinary skill given the teachings of the present principles provided herein, while maintaining the spirit of the present principles.

FIGS. 3-4 show an exemplary method 300 for translating different clinical protocols for particle therapy into a set of constraints, in accordance with an embodiment of the present principles.

The method 300 converts generic clinical criteria into a set of minimum-maximum constraints.

It is to be noted that method 300 can utilize a combination of quick treatment planning (per step 330) and a beamlet and/or voxel analysis (per step 320). The beamlet and/or voxel analysis can be based on, for example, the quick treatment planning results and/or the data (provided per step 310).

At step 310, obtain data including but not limited to clinical protocols, structure data, and scanning beam data.

The scanning beam data can be from an analytic model and/or a simulation. The scanning beam data provides information as to the dose deposited in each voxel given the input source of radiation. A tumor can be referred to as a target volume, such as clinical target volume (CTV), scanning target volume (STV), and planning target volume (PTV), while parts of the healthy tissue to be avoided are termed Organs at Risk, or OARs. We use the term "target structure" herein to refer to both cancer target volumes as described above and healthy tissue volumes, i.e., OARs. The structure data provides a labeling of voxels according to structure membership. The structures can be those referred to in the clinical protocols and may include Organs At Risk (OARs), and so forth. Each voxel corresponds to a known location in the 3D patient volume.

Scanning beam data can provide accumulated results of dose calculations, which in turn can be output from particle simulation. Particle-simulation-based dose calculation would commonly be done using a given number of particles for each beamlet. That number of particles corresponds to a duration of the beamlet at a given current (current is particles per time). Accumulated results can be provided, for example, as a dose per voxel per beamlet.

Typically, the duration to apply a beamlet at a given current would be chosen during a treatment plan. The scanning beam data would typically be calculated before those durations are chosen but, especially where the same number of particles have been simulated for each beamlet, the scanning beam data can give an indication of dose that will occur under treatment plans, e.g., if scanning beam data shows no energy deposited into a given voxel, it is very unlikely that any treatment plan utilizing those beamlets will deposit energy into the voxel (assuming a large enough number of simulated particles). So, although eventual doses will be modified by the beamlets' durations at a given current chosen during treatment planning, the scanning beam data can be used to get rough dose amounts, correlations, etc., as a basis for beamlet and voxel analysis.

At step 320, perform a beamlet analysis and/or a voxel analysis. Beamlet analysis evaluates beamlets based on beamlet criteria, such as importance (see below) and similarity of by-voxel energy deposited by the beamlet to that of other beamlets, for example, according to scanning beam data. An example of beamlet analysis is to check whether beamlet $B_i$'s dose contribution to voxels can be expressed as a linear combination of the dose contribution to voxels of other beamlets ($B_1, \ldots B_j$). A voxel analysis evaluates voxels based on voxel criteria, such as dose per voxel according to scanning beam data and similarity of the response of a voxel to beamlets to that of other voxels to the same beamlets. Voxel analysis also evaluates voxel geometry criteria, such as the spatial relationship with other voxels in the same structure; the spatial relationship with the boundary of the structure; and the spatial relationship with other voxels in different structures. An example of voxel analysis is to check whether voxels Vi and Vj get doses which are proportional or nearly proportional to each other for many or all possible treatment plans. The beamlet and/or voxel analysis can be based on results of a quick run of treatment planning, e.g., voxels likely to get low doses can be identified based on getting a low dose in the results of one or more quick treatment planning runs.

Another example of beamlet analysis can be selecting protobeams, for example, by performing a non-negative principal components analysis on the matrix that includes scanning beam data represented as dose deposited into each voxel by each of b beamlets and extracting as protobeams the first pb (pb<b) columns of the rotated data matrix calculated by multiplying the scanning beam data matrix times the rotations matrix that is output from the non-negative principal component analysis operation. Then as an example of voxel analysis, voxels can be evaluated based on their correlations in the reduced matrix.

At step 330, determine a quick run of treatment planning. The quick run of treatment planning can be based on the results of the beamlet analysis and/or voxel analysis or independent of such analysis. An example of a quick run of treatment planning can be based on a lookup table pre-calculated by matching the depth of the Bragg peak of a beamlet and the depth of a voxel of a target. The beamlets analyzed can be chosen, for example, based on a beamlet analysis that focuses on beamlet importance, as described below. Another example a quick run of treatment planning is a regression-based treatment planning using a small number of protobeams, where protobeams provide a reduced version of scanning beam data.

Note either or both of steps 320 and 330 can be performed and the results of one can be used as a basis for the other.

At step 340, for each structure, perform clustering considering all clinical protocols pertaining to the structure. For example, each structure may be associated with more than one protocol. As a particular example, a liver as an OAR may have two protocols associated with it, namely (i) the maximum dose of any voxel inside liver has to be lower than 37 Gy, and (ii) the median dose for the liver has to be lower than 25 Gy.

In an embodiment, step 340 includes step 340A.

At step 340A, for each clinical protocol, for each target structure, select proper (that is, "proper" in the mathematical sense, meaning cannot include the whole set) subsets (clusters) of voxels in the target structure and assign each of them a minimum-maximum constraint. In an embodiment, the voxel selection is based on at least one of: (1) the spatial relationship with other voxels in the same structure; (2) the spatial relationship with the boundary of the structure; (3) the spatial relationship with other voxels in different structures; (4) correlation among the voxels in the dose value for the radiation beamlets; (5) a dose determined from quick/estimated optimization results or optimization results from a previous run of treatment planning step; and (6) a shared response to a certain beamlet or set of beamlets. The preceding six exemplary bases for voxel selection can be considered to form clustering criteria. Moreover, other clustering criteria can also be used, while maintaining the spirit of the present principles.

Regarding item (6) of step 340A, namely a shared response to a certain beamlet, an example of using beamlet analysis to do clustering is to identify one or more beamlets which we believe are important. For example, based on analysis of scanning beam data (e.g., acquired as accumulated results of dose calculation where each beamlet was simulated with an adequate number of particles), a certain beamlet could be the only one that deposits energy above a threshold into a voxel of the target volume. Since that beamlet will likely be selected for any treatment plan, there is an increased likelihood versus random that voxels on that beamlet's path, in particular the part of the path where the beamlet is likely to deposit its energy (Bragg peak), will receive similar doses. Therefore, select voxels into which that beamlet deposits energy over a threshold to be in a cluster. This is an example of the sixth exemplary basis above, shared response to a certain beamlet. Quick treatment planning can also be used to choose important beamlets where, for example, important beamlets are those chosen to be included in the treatment plan with duration at a given current over a threshold. As an alternative to clustering voxels that receive a dose over a threshold on an important set of beamlets, voxels whose doses are correlated with one another on those beamlets can be clustered.

For each voxel, there may be multiple minimum-maximum constraints generated. We combine all the minimum-maximum constraints so that the resultant minimum-maximum is the most restricted, and it fulfils all the minimum-maximum constraints generated. For example, for a voxel $V_i$, assume the generated minimum-maximum constraints are (i) min($V_i$)=20, max($V_i$)=50; and (ii) min($V_i$)=30, max ($V_i$)=55. The combined minimum-maximum constraints will become min($V_i$)=30, max($V_i$)=50. There may exist a set of generated minimum-maximum constraints for a particular voxel that conflict with each other, e.g., (i) min($V_i$)=20, max($V_i$)=50; and (ii) min($V_i$)=55, max($V_i$)=75. In this case, it is impossible to combine these constraints and the system will report and prompt the user to review the inputs. Possible actions include re-clustering with changed parameters on the selection criteria, for example, relative to the six exemplary bases described herein above.

Regarding item (4) of step 340A, namely correlation among the voxels in a dose value for the radiation beamlets, one good example is that if voxels $v_i$ and $v_j$ have a similar dose value for all the possible beamlets, one should not set the minimum constraint of $v_i$ much higher than the maximum constraint of $v_j$. Otherwise, it is very unlikely any treatment plan can fulfill such constraints. In this case, the present principles will put voxels $v_i$ and $v_j$ in the same cluster so that they will have a similar minimum-maximum constraint.

Regarding item (5) of step 340A, namely a dose value determined from quick/estimated optimization results, one good example is to look at an estimated plan generated by a look up table or a quick optimization algorithm, which can be over hundreds of times faster than the actual treatment planning algorithm. From the estimated plan, if voxels $v_i$ in a structure outside the target volume receive a high dose relative to other voxels in the structure, we may want to set a slightly higher minimum constraint for those voxels. Doing so may increase the likelihood of finding a feasible solution. That is why we would like to cluster $v_i$ separately from the other nearby voxels with a different dose level(s) from the estimated plan.

At step 350, for each cluster, assign a minimum-maximum constraint. Assigning a constraint to a cluster means assigning the same constraint to each of the individual voxels in the cluster. The constraint expresses a bound on the total dose to a voxel during treatment according to a treatment plan. In an embodiment, the constraint is assigned based the protocol and the relationship between the clusters. The minimum-maximum constraints are assigned such that if they are satisfied, the constraints of the original protocol are satisfied. For example, assume the clinical protocol of a structure is to have a mean dose smaller than 30 Gy. In this case, step 340A can create 5 clusters ($C_1$, $C_2$, $C_3$, $C_4$, and $C_5$) for that particular structure. We can set some clusters (e.g., $C_4$ and $C_5$) to have a higher maximum constraint and some clusters (e.g., $C_1$, $C_2$, and $C_3$) to have a lower maximum constraint such that the overall mean dose of all 5 clusters is still lower than the goal of 30 Gy. One exemplary reason for setting higher maximum constraints to some clusters (e.g. $C_4$, $C_5$) is that they may be very close to the tumor.

At step 360, run the actual treatment planning optimization algorithm, using the minimum-maximum constraints (in place of the clinical protocol from which the minimum-maximum constraints were determined). In an embodiment, system 100 of FIG. 1 performs the optimization algorithm and returns the best treatment plan based on the inputs.

At step 365, determine if the treatment plan quality is sufficient. Typically, here the treatment plan can be measured against the original clinical criteria, i.e., not the minimum-maximum criteria created in step 350. If so (quality is sufficient), then proceed to step 370. Otherwise (quality not sufficient), proceed to step 366.

At step 366, identify any shortcoming in the radiation treatment planning problem solution that results in the quality not being determined as sufficient.

Next proceed to one of steps 320, 330 or 340. In other words, perform another beamlet and/or voxel analysis and/or do another quick run of treatment planning and then re-cluster, or re-cluster based on the results of the treatment plan without going through either of step 320 or step 330. Use of the treatment plan results to guide re-clustering could be similar to use of the quick treatment planning results (step 330) and/or additionally incorporate knowledge of the existing clusters. E.g., re-clustering could focus on clusters all or some of whose member voxels fail to meet minimum-maximum constraints of step 350. In some cases, the same clustering as the previous iteration may be used but constraint assignments adjusted (step 350).

At step 370, perform a radiation therapy procedure on a patient, based on the resultant plan from step 360. In an embodiment, system 200 of FIG. 2 performs the radiation therapy procedure of step 370 of method 300 of FIG. 3. Of course, other types of radiation therapy/radiation emitting systems can also be used in accordance with the teachings of the present principles while maintaining the spirit of the present principles.

Figure 5:
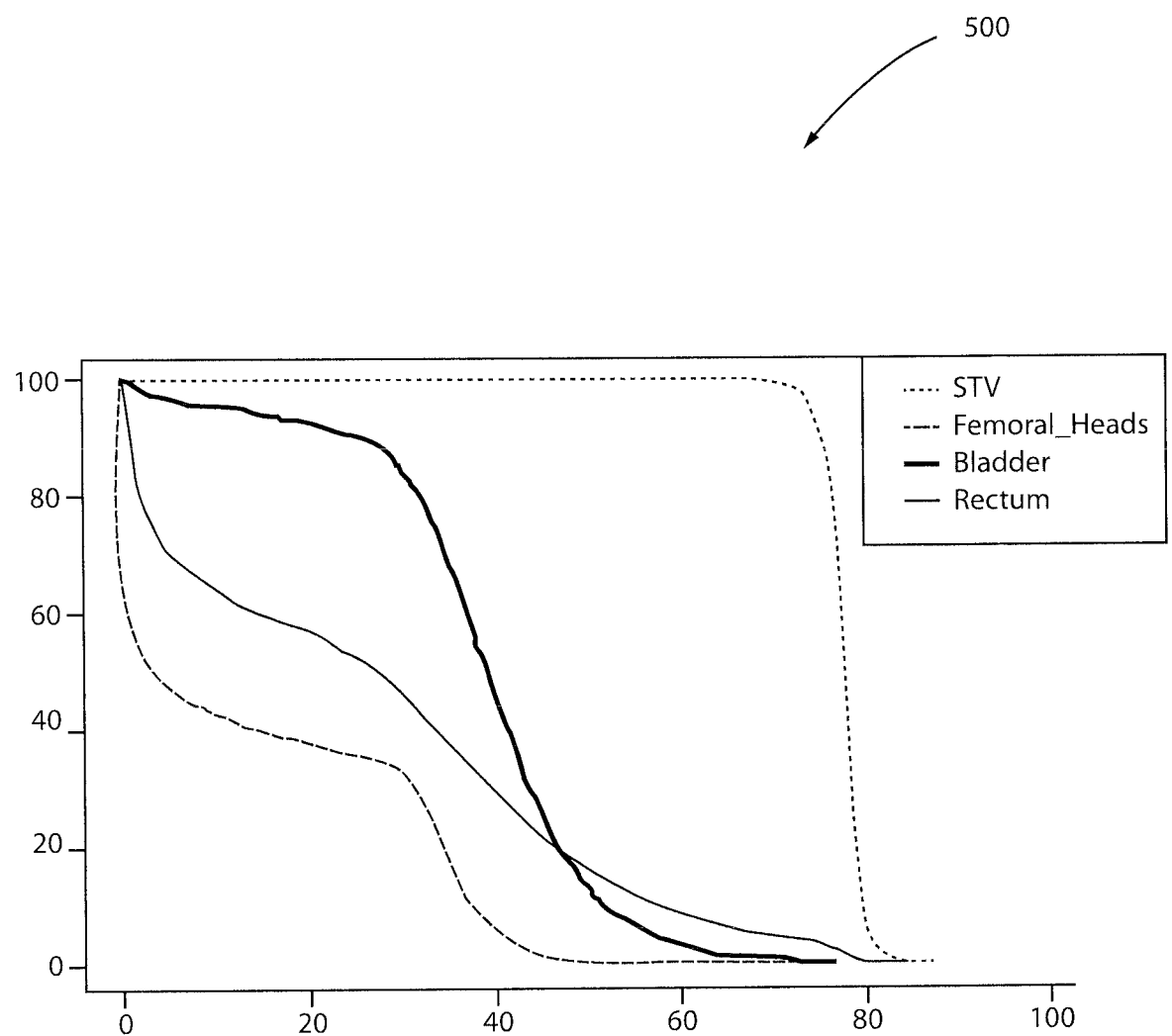
FIG. 5 shows an exemplary dose-volume histogram curve 500, in accordance with an embodiment of the present principles.

Each radiation beamlet deposits a dose at various voxels in one or more target structures. Each voxel has a sum dose. One or more Dose-Volume-(integral)-Histogram curves, and/or other representations, can be used to summarize the dose distribution of each structure. As an example voxel dose, consider the following: the voxel at the 60-percentile in the bladder has a total dose of 37 Gy. FIG. 5 shows an exemplary dose-volume histogram curve 500, in accordance with an embodiment of the present principles. The histogram curve 500 includes curves for a STV, femoral heads, bladder, and rectum.

It is to be appreciated that there are many forms in which clinical criteria can be provided for use by the present principles. As examples, and certainly not to be construed as limiting, the present principles can be applied to any of the following types of clinical criteria: minimum and maximum; median (50 percentile); mean; volume (e.g., V>30 Gy<50%: Volume with dose>30 Gy is less than 50% of the total volume); and dose (e.g., $D_{95\%}$>75 Gy: Dose of the voxel at the 95 percentile is greater than 75 Gy). These can be in the format of a constraint (e.g., a volume constraint, a mean dose constraint, a median dose constraint, a percentile dose constraint, and so forth). Further example volume constraints include, but are not limited to: "V(>X Gy)≤Y %"; "V(<X Gy)≤Y %"; "V(>X Gy)>Y %"; "V(<X Gy)>Y %"; and so forth.

A description will now be given regarding a mean dose of a target structure, in accordance with an embodiment of the present principles.

In an embodiment, a mean dose can be calculated as follows:

$$\Sigma(Dijk*Iijk,S)/\Sigma(Iijk,S)$$

where Dijk denotes the dose at voxel (i,j,k), and Iijk,S={0,1} to identify whether voxel (i,j,k) is in structure S and the sums are taken over the set of all voxels.

In an embodiment, we transform the upper limit U of the mean to a set of minimum-maximum constraints. In an embodiment, the transformation involves clustering the structure based on a combination of the following criteria: voxels assigned into a cluster are neighbors; and/or voxels assigned into a cluster have certain similarity among their doses for each radiation field, e.g., based on scanning beam data. Note this gives examples of items 1 and 4 of step 340A.

In an embodiment, for each cluster Cm, set the upper limit Um such that the following applies.
(1) Even if all the voxels in each cluster reach the upper limit, the mean dose of the whole structure is still bounded by Um.
(2) This guarantees it always honor the upper bound, but always pessimistic.
(3) Alternatively, we can loosen Um a little bit for those clusters which are not strongly correlated with the others.
(4) Adjust each Um based on the relationship between clusters.

Figure 6:
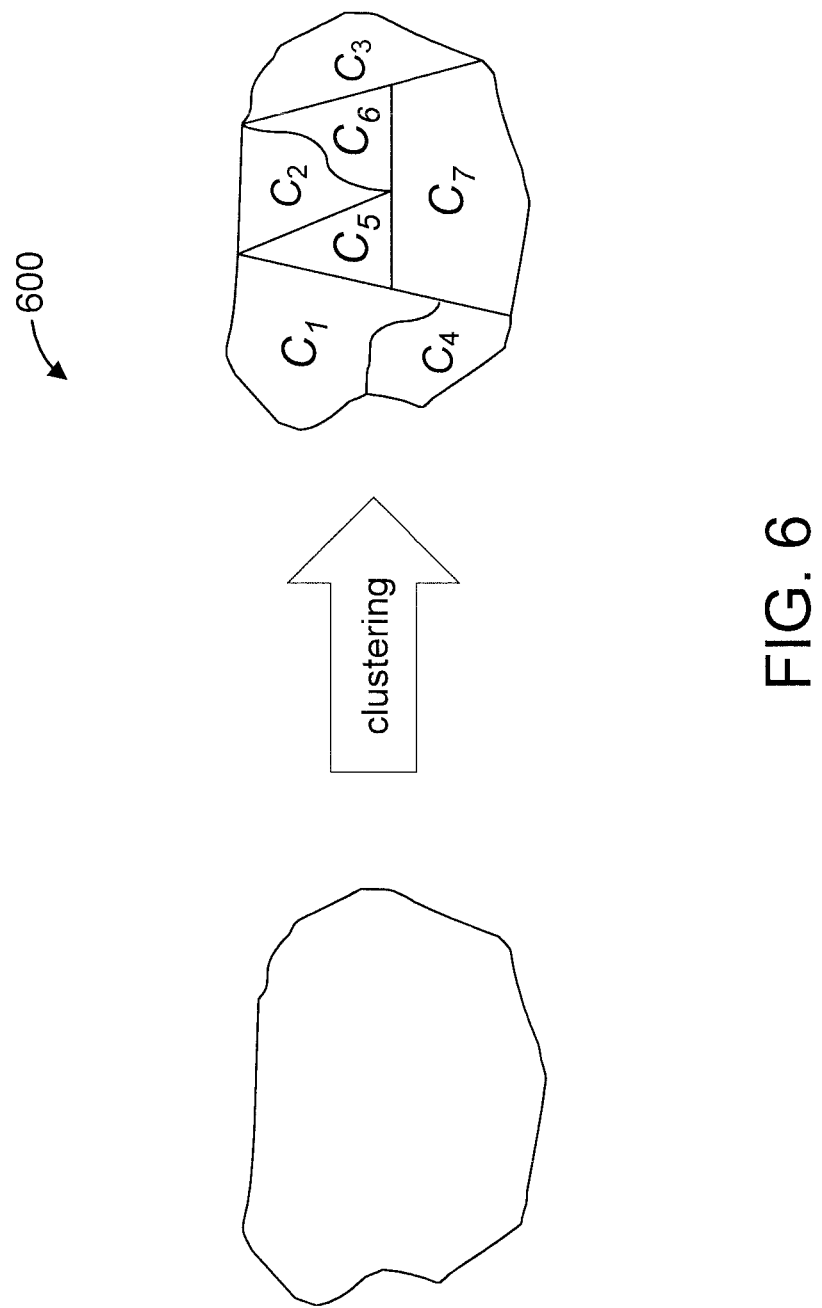
FIG. 6 shows an exemplary clustering 600 of a target structure to which the present principles can be applied, in accordance with an embodiment of the present principles.

FIG. 6 shows an exemplary clustering 600 of a target structure to which the present principles can be applied, in accordance with an embodiment of the present principles. In an embodiment, the target structure is clustered into 7 clusters, namely C1 through C7.

Assume Mean dose of target structure by volume is set to be <=30. The following is a naïve example of the clustering 600 and assignment of minimum-maximum constraints to clusters:
max(C1)=max(C2)=max(C3)=max(C4)=max(C5)=max(C6)=max(C7)=30.

In other words, the maximum dose of each voxel in each cluster is constrained to be 30. The following is a better example of the clustering 600 and assignment of minimum-maximum constraints to clusters:
max(C1)=max(C2)=max(C3)=max(C5)=max(C6)=max(C7)=25;
max(C4)=68; and such that [25*volume(C1 U C2 U C3 U C5 U C6 U C7)+68*volume(C4)]/(volume of all 7 clusters) ≤30, where "U" denotes a union operation in set theory in the preceding equation.

It is to be noted that setting max(C4)=68 is due to the fact that a target structure (tumor) is immediately next to C4 and setting max(C4)=30 generates a planning problem with no solution. This is an example of item (3) of step 340A.

A description will now be given regarding volume constraints of a structure, in accordance with an embodiment of the present principles.

The volume constraints will be described with respect to the following example:

$$V(>30Gy) \le 50\%,$$

which denotes a volume with dose >30 Gy is less than or equal to 50% of the total structure volume.

The volume constraint is transformed to a set of minimum-maximum constraints as follows. Select voxels that make up 50% of the volume in the structure based on (1) voxels deep inside the structure (far from other structures) (this is an example of item (2) of step 340A); and (2) voxels with a low dose based on each radiation field. Of course, the preceding criteria is illustrative and, thus, other criteria can also be used. The selected voxels form a cluster. For each of the selected voxels, set the upper limit to 30 Gy.

Perform a similar translation for the lower bound, when another protocol is in the format of "V(<30 Gy)≤50%", as follows: select voxels that make up 50% of the volume and set the lower bound for each voxel in the cluster to 30 Gy, so that the volume with a dose equal to or greater than 30 Gy is more than 50%.

Perform a similar translation for the percentile dose constraints. For example, for the following dose of D95%>75 Gy (that is, a dose of the voxels at the 95 percentile is greater than 75 Gy), select 95% of voxels in the structure and set the lower limit for each voxel in that cluster to 75 Gy.

A description will now be given of cluster selection based on a rough planning, in accordance with an embodiment of the present principles. Referring to method 300, the clustering step 340 is performed based on the results of the quick run of treatment planning determined at step 330.

A rough (e.g., quick) treatment plan is generated (per step 330) based on, for example, a look-up table, and/or an approximated optimization (Linear Programming (LP), Goal Programming (GP), regression, and so forth.

Voxels are clustered into subsets (per step 340). For example, cluster voxels whose doses are significantly lower than (e.g., by a pre-specified margin or percentage) the doses of other voxels in the same structure and/or voxels whose doses are significantly higher than doses of other voxels in the same structure (this is an example of item (5) of step 340A). For an OAR, then, for example, for some protocols, the clusters containing voxels with relatively high doses can be assigned a relaxed (high) upper bound, since it may be difficult to avoid dosing those voxels, which in turn may be because they are near the tumor.

A description will now be given of some of the many attendant benefits of the present principles.

One benefit is the conversion of all clinical protocols into simpler minimum/maximum constraints in the optimization. Another benefit is that while not all optimization algorithms can naturally handle all the clinical protocols, many of the existing optimization algorithms can handle minimum/maximum constraints. Yet another benefit is the conversion of target structures into clusters, which may simplify the problem and can improve the quality of the results and speed up the optimization runtime.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Having described preferred embodiments of a system and method (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for converting clinical criteria constraints for a target structure of radiation therapy into a second set of constraints, the method comprising:
    selecting, by a hardware processor, a plurality of clusters of voxels in the target structure based on pre-specified criteria in a form of clinical criteria constraints on a radiation dosage;
    assigning, by the hardware processor, each of the plurality of clusters of voxels a respective constraint that specifies one or more bounds on a radiation dose applied to each voxel in a corresponding one of the plurality of clusters of voxels; and
    storing, in a memory device, the respective constraint for each of the plurality of clusters of voxels as the second set of constraints.

2. The method of claim 1, wherein the one or more bounds comprise a zero bound corresponding to the minimum constraint and an infinity bound corresponding to the maximum constraint, the zero bound and the infinity bound for implementing an absence of the minimum constraint and the maximum constraint.

3. The method of claim 1, wherein the clinical criteria constraints converted into the second set of constraints are in a format of at least one of, a mean dose constraint, a median dose constraint, and a percentile dose constraint.

4. The method of claim 1, wherein different constraints are assignable for different ones of the plurality of clusters of voxels in the target structure.

5. The method of claim 1, wherein said selecting step performs voxel selection based on at least one of, a spatial relationship with other voxels in a same structure, a spatial relationship with a boundary of the target structure, and a spatial relationship with other voxels in one or more different structures.

6. The method of claim 1, wherein said selecting step performs voxel selection based on at least one of, a correlation among the voxels in a dose value for radiation beamlets, and a dose value determined from optimization results.

7. The method of claim 1, further comprising performing a beamlet analysis to generate cluster selection data for selecting at least some of the plurality of clusters of voxels.

8. The method of claim 1, further comprising performing a voxel analysis to generate cluster selection data for selecting at least some of the plurality of clusters of voxels.

9. The method of claim 1, further comprising performing an estimated treatment planning to generate cluster selection data for selecting at least some of the plurality of clusters of voxels.

10. The method of claim 1, wherein said selecting step is performed based on at least one of, structure data for one or more target volumes, structure data for one or more organs at risk, clinical protocol data, and scanning beam data from an analytic model or a simulation.

11. The method of claim 1, wherein the respective constraint on at least one of the plurality of clusters of voxels is assigned based on a clinical protocol and a relationship between the at least one of the plurality of clusters of voxels with respect to at least one other one of the plurality of clusters of voxels.

12. The method of claim 1, wherein said selecting step clusters the target structure based on at least one of, voxels in a same cluster being neighbors and the voxels in the same cluster having a high correlation for one or more radiation fields.

13. The method of claim 1, further comprising performing, by a radiation therapy machine, a radiation therapy procedure on a patient using a treatment plan calculated by using the respective constraint for each of the plurality of clusters of voxels as inputs to the treatment plan.

14. A computer program product for converting clinical criteria constraints for a target structure of radiation therapy into a second set of constraints, the computer program product comprising a computer readable storage medium having program instructions embodied therewith, the program instructions executable by a computer to cause the computer to perform a method comprising:
    selecting, by a hardware processor, a plurality of clusters of voxels in the target structure based on pre-specified criteria in a form of clinical criteria constraints on a radiation dosage;
    assigning, by the hardware processor, each of the plurality of clusters of voxels a respective constraint that specifies one or more bounds on a radiation dose applied to each voxel in a corresponding one of the plurality of clusters of voxels; and
    storing, in a memory device, the respective constraint for each of the plurality of clusters of voxels as the second set of constraints.

15. The computer program product of claim 14, wherein said selecting step performs voxel selection based on at least one of, a spatial relationship with other voxels in the same structure, a spatial relationship with a boundary of the target structure, and a spatial relationship with other voxels in one or more different structures.

16. The computer program product of claim 14, wherein said selecting step performs voxel selection based on at least one selected from the group consisting of, a correlation between other voxels in a dose value for radiation beamlets, and a dose value determined from optimization results.

17. The computer program product of claim 14, further comprising performing at least one of, a beamlet analysis, a voxel analysis, and an estimated treatment planning, to generate cluster selection data for selecting the plurality of clusters of voxels.

18. The computer program product of claim 14, wherein said selecting step is performed based on at least one of, structure data for one or more target volumes, structure data for one or more organs at risk, clinical protocol data, and scanning beam data from an analytic model or a simulation.

19. The computer program product of claim 14, wherein the clinical criteria constraints converted into the second set of constraints are in a format of at least one of, a mean dose constraint, a median dose constraint, and a percentile dose constraint.

20. A system for converting clinical criteria constraints for a target structure of radiation therapy into a second set of constraints, the system comprising:
    a hardware processor for selecting a plurality of clusters of voxels in the target structure based on pre-specified criteria in a form of clinical criteria constraints on a radiation dosage, and assigning each of the plurality of clusters of voxels a respective constraint that specifies one or more bounds on a radiation dose applied to each voxel in a corresponding one of the plurality of clusters of voxels; and a memory device for storing, the respective constraint for each of the plurality of clusters of voxels as the second set of constraints.

* * * * *